United States Patent [19]

von Gierke et al.

[11] Patent Number: 4,511,228

[45] Date of Patent: Apr. 16, 1985

[54] MEASUREMENT OF VISUAL CONTRAST SENSITIVITY

[75] Inventors: Henning E. von Gierke, Yellow Springs; Adolf R. Marko, Fairborn, both of Ohio

[73] Assignee: The United States of America as represented by the Secretary of the Air Force, Washington, D.C.

[21] Appl. No.: 403,247

[22] Filed: Jul. 29, 1982

[51] Int. Cl.³ ............................................... A61B 3/02
[52] U.S. Cl. ..................................... 351/243; 351/237
[58] Field of Search ............... 351/239, 240, 241, 242, 351/243, 244, 237

[56] References Cited

U.S. PATENT DOCUMENTS 3,737,217  6/1973  Haines et al. ........................ 351/23
4,293,200 10/1981  Dobson et al. ...................... 351/243

OTHER PUBLICATIONS

"Operating Instructions for Midgard CRT Controller", Midgard Electronics.
Optronix Corp. Operating Manual for Series 200 Vision Tester—5/81.
AFAMRL-TR-80-121, Arthur P. Ginsburg, "Proposed New Vision Standards for the 1980's and Beyond: Contrast Sensitivity", 9/81.

*Primary Examiner*—Rodney B. Bovernick
*Attorney, Agent, or Firm*—Donald J. Singer; Bernard E. Franz

[57] ABSTRACT

This invention involves measurement of the visual contrast sensitivity (modulation transfer) function of a human subject by means of a linear or circular spatial frequency pattern on a cathode ray tube whose contrast is automatically decreasing or increasing depending on the subject pressing or releasing a hand-switch button. The threshold of detection of the pattern modulation is found by the subject by adjusting the contrast to values which vary about the subject's threshold thereby determining the threshold and also providing by the magnitude of the contrast fluctuations between reversals some estimate of the variability of the subject's absolute threshold. The invention also involves the slow automatic sweeping of the spatial frequency of the pattern over the spatial frequency spectrum of interest; or the stepwise switching to specific selected discrete frequencies after preset time intervals or after threshold has been defined at each frequency by a selected number of subject-determined threshold crossings; i.e., contrast reversals.

17 Claims, 7 Drawing Figures

MEASUREMENT OF VISUAL CONTRAST SENSITIVITY

RIGHTS OF THE GOVERNMENT

The invention described herein may be manufactured and used by or for the Government of the United States for all governmental purposes without the payment of any royalty.

BACKGROUND OF THE INVENTION

The field of the invention relates to the measurement of visual sensitivity of contrast as a function of spatial frequency.

It is worth noting the contrast between testing techniques used to evaluate human sensory responses. In particular, note the disparity between testing of the visual and auditory senses. It is generally known that the standard test for the measurement of auditory acuity consists of presenting a sequence of audio signals, which vary in both amplitude and frequency, to acertain the threshold of audio sensitivity. An automated version of this testing technique was introduced by G. von Bekesy (ACTA OTO-LARYNGOL, 35:411 (1947)), and led to the various types of Bekesy audiometers or automatic audiometers to test hearing. On the other hand, conventional visual examinations singularly rely upon Snellen or similar type acuity charts, in near-total oblivion to the concurrent effects of contrast sensitivity and spatial frequency of visual acuity. Since the Snellen type acuity test consists of letters, typically L or E, set in a highly contrasted background, and these letters consist of luminance variations in terms of amplitude and spatial frequency over a very limited range, defined by the letter shape and size, it fails to adequately consider the functional relationship between contrast sensitivity and spatial frequency on visual acuity.

Advanced artisans have come to recognize the importance of the interrelationship between contrast sensitivity and spatial frequency in the visual process. Though the link is known, the difficulty in testing for these parameters in a simple, rapid, quantifiable manner has prevented widespread implementation.

An article by L. Ronchi et al, "Some Remarks on Opthalmic Test Types" in the American Journal of Optometry and Archieves of American Academy of Optometry, June, 1972, pp. 491-496 (copy in class 351/32) discusses some basic problems concerning visual test charts, such as size progression and target selection. He refers to an article by Kelly, "$J_o$ Stimulus Pattern for Visual Research" J. Opt Soc. Am., 50 (11)1115-1116, 1960 on a test pattern comprising concentric circles which can differ from one another in frequency and/or modulation depth.

A. P. Ginsburg has a pending patent application Ser. No. 282,997 filed July 14, 1981, now U.S. Pat. No. 4,365,873, for a "Spatial Frequency and Contrast Sensitivity Test Chart" and a corresponding report AFAMRL-TR-80-121 on "Proposed New Vision Standards for the 1980's and Beyond: Contrast Sensitivity". Each includes a figure showing examples of sine-wave gratings with low, medium, and high spatial frequencies at low and high contrast, and also includes definitions of spatial frequency and contrast. It is noted that the gratings will have different visibilities depending upon viewing distance due to the visual filtering characteristics of the observer. The Ginsburg patent application and report are hereby incorporated by reference.

R. F. Haines, U.S. Pat. No. 3,737,217 for "Visual Examination Apparatus", covers an automated apparatus for measuring visual sensitivity and mapping blind spot location. It includes a projection system for displaying to a patient a series of visual stimuli, a response switch enabling him to indicate his reaction to the stimuli, and a recording system (a two-pen plotter) responsive to both the visual stimuli per se and the patient's responses.

SUMMARY OF THE INVENTION

An object of the invention is to simplify the measurement of visual contrast sensitivity without the need for a specialized laboratory. Another object is to provide higher speed and economy of threshold measurements.

One of the main characteristics of the invention is an automatically decreasing or increasing contrast of a stimulus pattern depending on the actuation of a switch controlled by the subject.

One feature is the automatic decreasing or increasing contrast of a display depending on the subjects response through a handheld switch or any other means (e.g., evoked cortical response).

Another feature is automatic sweeping of a spatial frequency stimulus as a function of time or automatic step-wise variation of frequency to cover a desired spatial frequency bandwidth Another feature is automatic plotting of contrast sensitivity in logarithmic, linear, or other scale on one coordinate and of continuously or step-wise varying spatial frequency on the other coordinate of a rectangular coordinate system.

DETAILED DESCRIPTION

Figure 1:
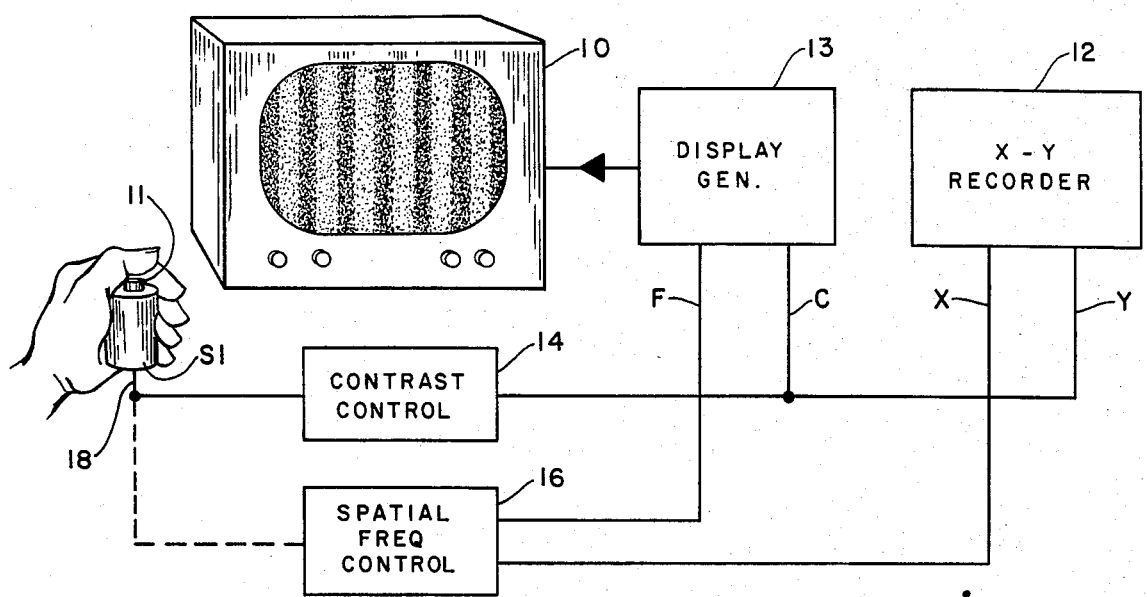
FIG. 1 is a system block diagram.

FIG. 1 is a block diagram of a system for measurement of the visual contrast sensitivity (modulation transfer) function of a human subject. It makes use of a monitor 10 and a display generator 13 providing a linear or circular spatial frequency pattern on a cathode ray tube (which could be a television monitor). The example shown is a linear display of vertical bars. The spatial frequency is controlled by a voltage on lead F and the contrast is controlled by a voltage on lead C. The system also makes use of a standard X-Y recorder, with voltages on leads X and Y determining the X and Y coordinates of a stylus.

The display generator 13 was specially constructed for an experimental system, but a commercial unit known as a Midgard CRT Controller is available from Midgard Electronics, Boston, Mass. For controlling a cathode ray tube display unit 10, the controller 13 outputs a sawtooth or ramp waveform as an X-axis sweep, a high frequency triangle waveform for Y-axis or line generation, and a sine, square, or triangle modulation as a Z-axis intensity control, for the purpose of generating grating or visual patterns. Thus, the display is a series of closely spaced vertical lines, which without modulation on the Z-axis would appear as a uniform illumination on the screen. The Z-axis module controls the pattern to modulate it in time. Contrast, luminance and spatial frequency are each set by dials. The output Z signal from the controller 13 to the display unit 10 provides both contrast and luminance information. Luminance is a DC offset—contrast is a symmetrical peak-to-peak waveform about that luminance level. The Z-axis circuitry contains a function generator for the production of sine, square, or triangle waveforms into the Z-axis intensity input of the CRT for the purpose of generating sine, square or triangle gratings. A switch selects which of sine, square, or triangle waveforms will be displayed. In general, a sine wave grating is preferred. The voltages on leads F and C in FIG. 1 are external signals for controlling the frequency and contrast produced by the Z-axis function generator (in place of the dials on the unit).

A contrast control circuit 14 connected, via a line 18 to a handheld switch S1 controls the voltage on lines C and Y. The voltage is automatically decreasing or increasing depending on the subject pressing or releasing a button 11 on switch S1. The switch may be a cylindrical unit held in the closed fist with the thumb on the button. A spring restores the switch to the normal open position when the button is released. The threshold of detection of the pattern modulation is found by the subject by adjusting the contrast to values which vary about the subject's threshold thereby determining the threshold and also providing by the magnitude of the contrast fluctuations between reversals some estimate of the variability of the subject's absolute threshold.

The spatial frequency control circuit 16 controls the voltages on lines F and X. Slow automatic sweeping of the spatial frequency of the pattern over the spatial frequency spectrum of interest may be provided by a circuit which varies the voltage on line F in a continuous manner from a minimum to a maximum value. The same voltage may be applied to lead X to move the pen of the recorder 12 along its X coordinate in a continuous linear manner. As an alternative, the spatial frequency may be stepwise switched to specific selected discrete frequencies after preset time intervals or after threshold has been defined at each frequency by a selected number of subject-determined threshold crossings; i.e., contrast reversals.

Figure 2:
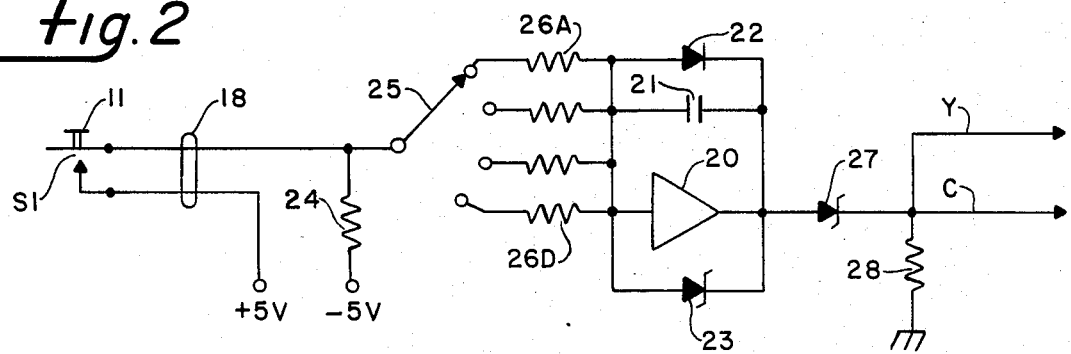
FIGS. 2 and 3 are alternative embodiments of the contrast control of FIG. 1.
Figure 3:
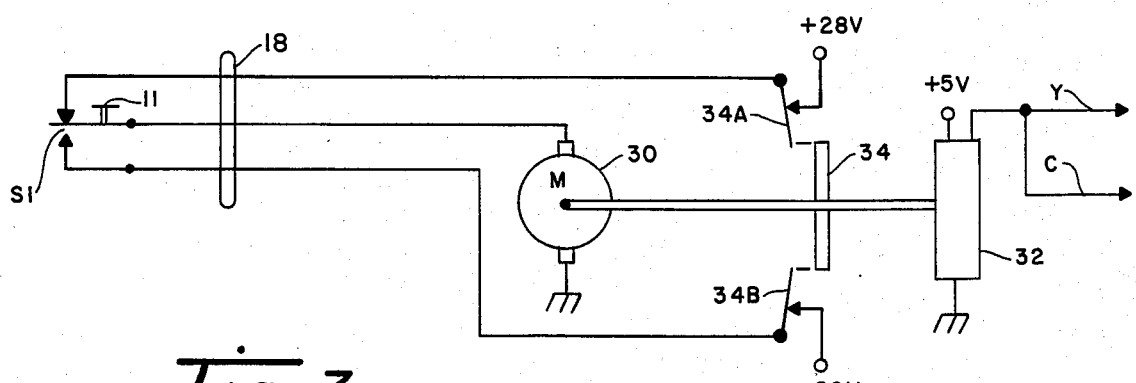

Automatic decrease or increase of the visual stimulus on the CRT of display unit 10 may be achieved with contrast control 14 either (a) electronically by a voltage decreasing or increasing automatically after each switch reversal as shown in FIG. 2, and thereby increasing or decreasing the stimulus contrast or (b) mechanically by a reversing attenuator motor, as shown in FIG. 3, operated by the subject switch controlling a stimulus contrast. In either case a voltage proportioned to the one controlling the stimulus contrast also controls the position of a recording stylus of recorder 12 thereby recording the contrast variation about the threshold as a function of time.

Figure 4:
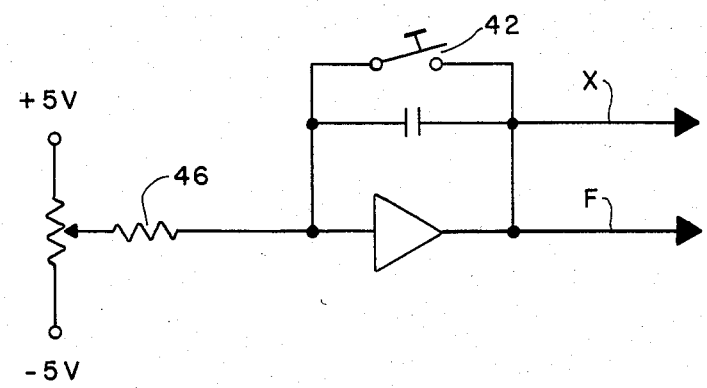
FIGS. 4 and 5 are alternative embodiments of the spatial frequency control of FIG. 1.

To obtain the contrast sensitivity function (threshold) as a function of frequency with spatial frequency control 16, either (a) the spatial frequency of the display is slowly continuously changed over the frequency range of interest as shown in FIG. 4, or (b) the spatial frequency of the display is automatically switched after a predetermined time period or after a selected number of threshold crossings to the next higher discrete spatial frequency selected until the total number of selected frequencies has been presented in ascending (or descending) sequence.

The automatic decreasing or increasing of the threshold contrast can be adjusted to different speeds selected by the experimenter. The typical range of threshold crossings achieved in this way might vary between five and twenty-five crossings per minute. However, slower or faster rates might be desirable depending on experimental purpose. In a laboratory model of the invention, the contrast was controlled as a logarithmic function of the linear varying control voltage. Three speeds of change have been provided: 3 dB/second, 6 dB/second and 12 dB/second. Different sets of speeds as well as a different function (instead of logarithmic) may be used.

The electronic embodiment of the contrast control circuit 14 shown in FIG. 2 includes an integrator comprising an operational amplifier 20 with a feedback capacitor 21 between its output and input. A diode 22 and a Zener diode 23 are connected in parallel with the capacitor. The switch S1 connected to the circuit via line 18 has one contact connected to a plus five-volt source and the other contact connected to the rotor of a multiposition switch 25 and also via a resistor 24 to a minus five-volt source. There are four resistors 26A-26D connected from respective contact positions of switch 25 to the input of the amplifier 20. A diode 27 connects the amplifier output to output lines Y and C. A resistor 28 is shunt connected from the output lines Y and C to ground.

If the subject switch S1 is open (button 11 not depressed), the minus five volts via resistor 24 and a selected one of resistors 26A-26D is applied to the input of the integrator. The output voltage will therefore increase at a rate determined by capacitor 21 and the selected resistor. If the Zener voltage of diode 23 (5 volt) is reached, no further increase takes place, the display indicates maximum contrast and the recorder maximum vertical deflection upward. If the subject closes switch S1, plus five volts on the input of the integrator causes the output voltage to decrease linear with time, and the contrast and the recorder vertical deflection decrease accordingly until the limit given by diode 22 (0.6 volt) is reached. In operation the subject will open and close switch S1 to keep the contrast continuously near the threshold of the pattern visibility while the spatial frequency changes continuously or in steps.

The electro-mechanical embodiment of the contrast control circuit 14 shown in FIG. 3 includes a reversing motor 30 which drives via a gear reduction a potentiometer 32. A cam 34 mounted on the motor shaft operates normally closed limit switches 34A and 34B to open the circuit at the limit of travel in the two directions, to thereby stop the motor within a predetermined range of rotation. For this embodiment switch S1 has both normally closed and normally open contacts, and line 18 has three conductors. The center contact is connected to the motor armature, the normally closed contact via contacts 34A to a plus 28-volt source, and the normally open contacts via contacts 34B to a minus 28-volt source. The potentiometer 32 has a resistor (not shown) connected between a plus five-volt source and ground, with a sliding contact connected to the output lines Y and C. The motor speed may be controlled by voltage control (not shown).

The electronic embodiment of the spatial frequency control circuit 16 shown in FIG. 4 provides a continuous control. It is an integrator having an operational amplifier 40 with a feedback capacitor 41 connected from the output to the input. A potentiometer 44 connected between plus and minus five-volt sources has a sliding contact connected via a resistor 46 to the amplifier input. The amplifier output is connected to lines X and F. A switch 42 when closed shunts the capacitor 41 to discharge it to provide an initial value of the output voltage. When switch 42 is opened, the output voltage of the integrator will go up or down depending on the setting of the potentiometer 44. The rate of change of the output voltage is determined by the values of the capacitor 41, resistor 46, and the setting of the potentiometer 44 (voltage). The linear ramp output voltage will control the X-axis deflection of the X-Y recorder 12 via line X and the spatial frequency of the display on unit 10 via line F. The X-axis on the recorder 12 thus represents a linear function of both spatial frequency and of time.

Figure 5:
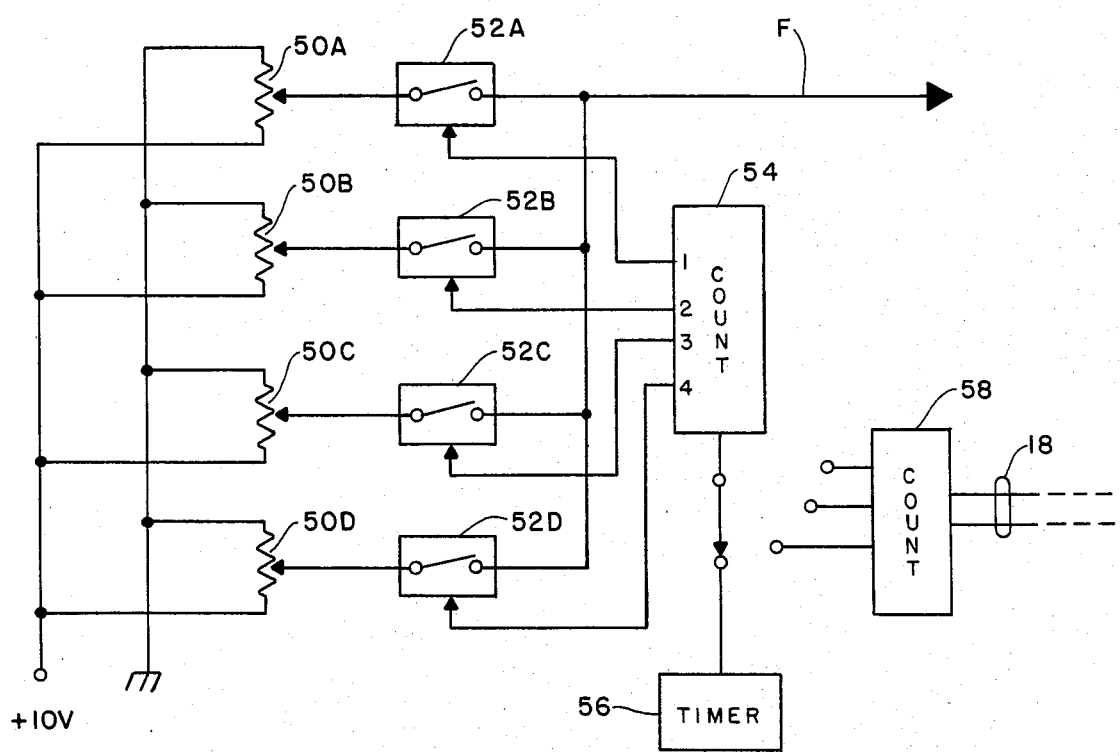

The embodiment of circuit 16 shown in FIG. 5 for producing a sequence of preset contrast spatial frequencies makes use of potentiometers and counters. Any number of potentiometers may be used, equal to the number of different frequencies desired for the display. The circuit shows four potentiometers 50A-50D, each connected between a plus ten-volt source and ground. The sliding contacts are connected via respective electronic switches 52A-52D to the output line F. The control inputs of the switches 52A-52D are connected to respective outputs of a counter 54, to be sequentially closed as the counter advances. The potentiometers 50A-50D are preset to produce four different spatial frequencies. To provide for predetermined equal time intervals at each frequency, a multiposition switch 55 is set to the output of a timer 56, which is adjustable for pulse duration and pulse frequency. If the frequency is to be advanced after a certain number of closings of switch S1 by the subject (threshold crossings), the switch 55 is set to one of the outputs of a decade counter 58. The input of this counter is connected via line 18 to switch S1, as indicated by the dashed line in FIG. 1. The number of threshold crossings is selected by switch 55, which is set to the desired output of counter 58. The number of different discrete spatial frequencies will depend on the particular experimental situation. While the spatial frequency of the display may be changed in discrete steps, it is still desired that the stylus of recorder 12 move in the X direction as a linear function of time. One way of doing this would be to connect line X to the circuit of FIG. 4 when line F is connected to the circuit of FIG. 5.

Figure 6:
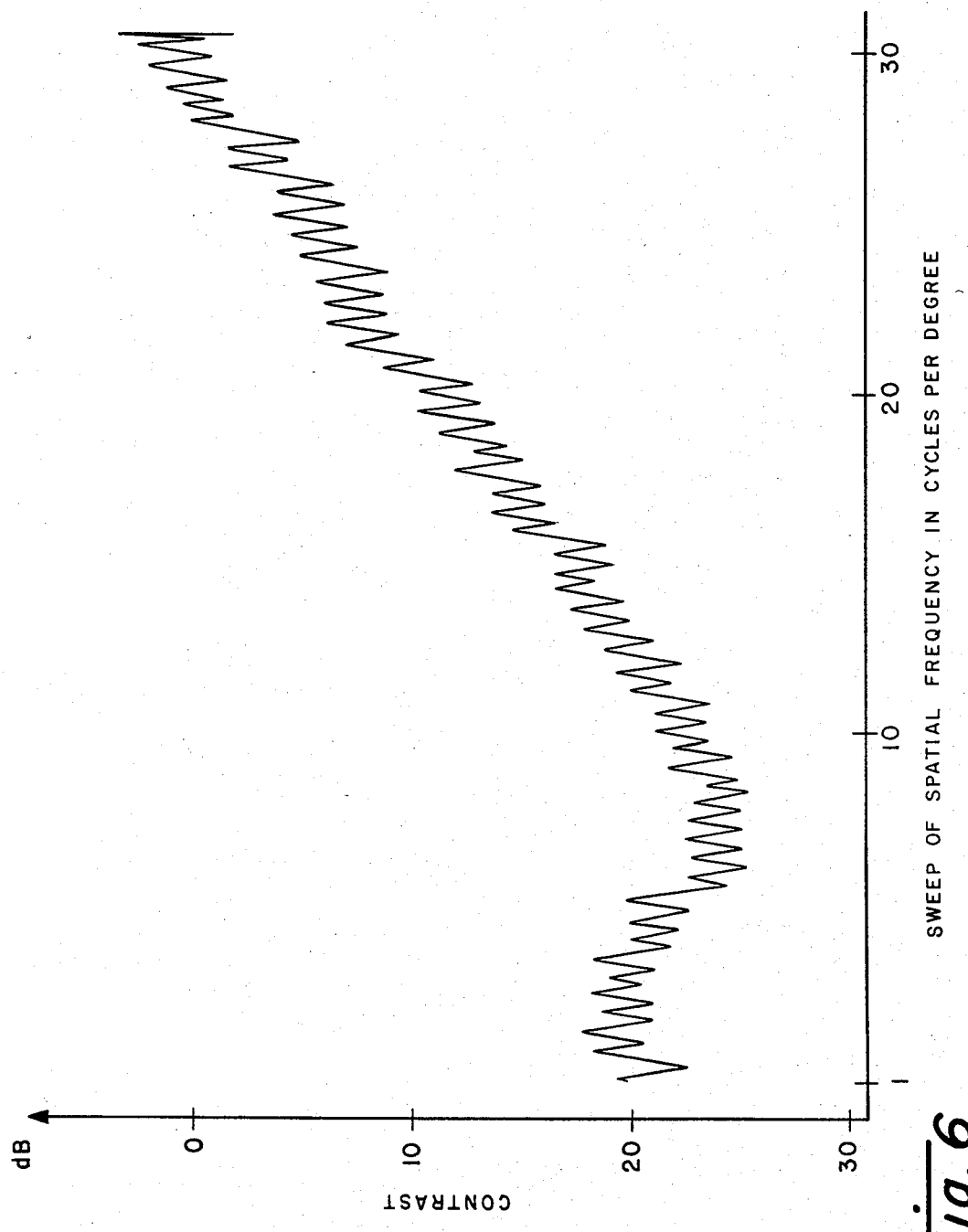
FIGS. 6 and 7 are representative of graphs produced by the X-Y recorder.
Figure 7:
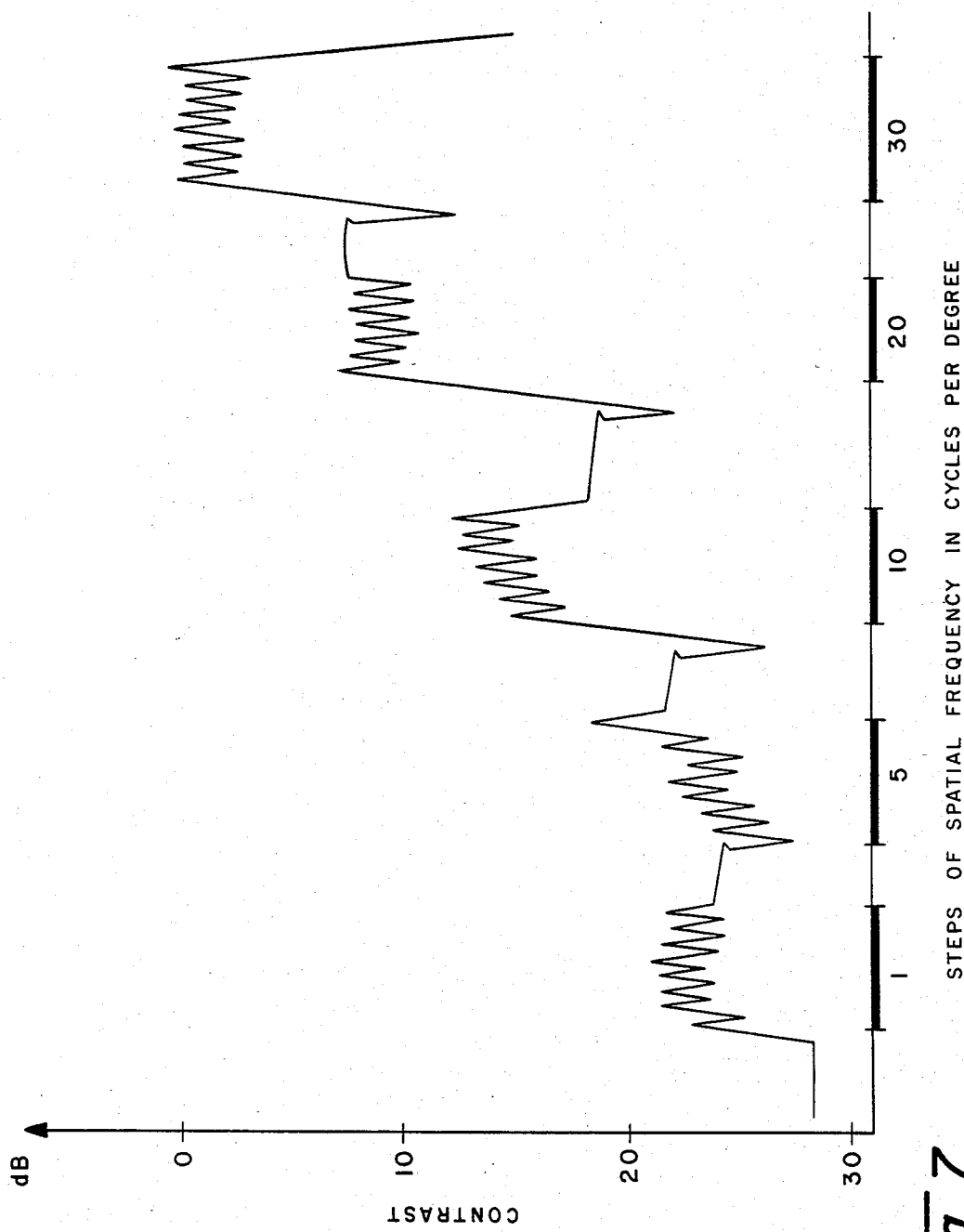

FIGS. 6 and 7 are actual examples of charts produced on the X-Y recorder 12. FIG. 6 shows a contrast sensitivity measurement using continuously changing spatial frequency, while FIG. 7 represents spatial frequency changes in steps using preselected frequencies. Note that the spatial frequency is given in cycles per degree (cpd), which is the number of bars seen in one degree of the field of view of the subject. This means that the eyes of the subject should be held at a predetermined distance from the display screen.

Display units using cathode ray oscilloscopes have been developed and are described in the literature, Dr. Christopher W. Tyler, Kettlewell Institute, 2232 Webster St., San Francisco, Calif. 94115. The Ginsburg patent application and report cited in the "Background" and incorporated by reference, provide a good description of the concept of measuring contrast sensitivity. In the report, after an Introduction and a section on "Present Visual Standards: Visual Acuity", he proceeds with a section on "Proposed Visual Standards: Contrast Sensitivity" the first part of which is quoted below. The names and dates in the quoted material relate to his list of references at the end of the report.

"Over the past decade, an alternate method of testing vision has come into use in both the scientific and clinical communities. The method measures visual sensitivity, using targets called sinewaves gratings, that are specified in terms of two variables: spatial frequency and contrast. Schade, 1956, pioneered the use of spatial frequency and contrast as a means of assessing spatial vision. Since then, a number of significant contributions have been made by other researchers—Delange (1958), Lowry and DePalma (1961), Westhiemer (1963), Kelly (1966), Robson (1966), Campbell and Green (1965)—that led to present methods for measuring contrast sensitivity. A sine-wave grating is a repeated sequence of light and dark bars that has a luminance profile, which varies sinusoidally about a mean luminance with distance. The width of one light and one dark bar of a grating is one cycle, or the period of the grating. The reciprocal of the period is the spatial frequency. Spatial frequency is expressed by the number of cycles of the grating that occur over a particular distance. The spatial frequency of an object can be expressed by cycles per object (cpo) dimension or, more commonly, by cycles per unit of visual angle. The number of cycles per object dimension is called normalized spatial frequency. It is determined by the size of the particular dimension of some part of the entire object and is independent of viewing distance. Cycles per unit of visual angle, more commonly called cycles per degree (cpd), is determined by the viewing distance. The luminance difference of the light and dark bars determines the contrast of the grating. The Michelson definition of contrast is most often used:

$$C = \frac{L_{max} - L_{min}}{L_{max} + L_{min}}$$

where $L_{max}$ and $L_{min}$ are the maximum and minimum luminances of the bars of the grating. Examples of sine-wave gratings having low, medium, and high spatial frequencies at low and high contrast are shown in FIG. 1. The luminance distribution for each grating is shown below each grating patch.

"If the contrast of a grating is increased from below its visibility to where the grating is just seen, then the grating is said to have reached threshold contrast. The reciprocal of the threshold contrast is called contrast sensitivity. Gratings of different spatial frequencies require different amounts of contrast to reach threshold for the observer. In a typical measurement session for contrast sensitivity, a subject adjusts the contrast of a sine-wave grating until the bars are just at the threshold of visibility. Measurements are repeated for a number of bar widths (spatial frequencies). The reciprocal of contrast threshold is plotted as a function of spatial frequency to create a contrast sensitivity function. A typical contrast sensitivity function is shown in FIG. 6. The broad, inverted U-shaped curve describes the visual "window" that limits the range of the size of objects that can be seen under conditions of threshold contrast. The area above the curve is the region of low contrast where the visual system does not see objects because it is below threshold. Note that the visual system is most sensitive to sine-wave gratings at about 2 cpd, depending upon experimental conditions. Sensitivity decreases for spatial frequencies above and below peak sensitivity. As with auditory processing of temporal frequencies, only a limited range of spatial information can be passed by the visual system. The physiological limit is about 60 cpd, which depends upon viewing conditions . . .

"There are three general techniques currently used to measure contrast sensitivity to gratings: electronic generation for TV displays (Campbell and Green, 1965), film (Ginsburg, 1977), and photographic plates (Arden and Jacogsen, 1978). The TV displays provide the most accurate measurements; however, high levels of expertise in electronics, display technology, and/or computer hardware and software are required for best results."

The references to FIG. 1 and FIG. 2 in the above quote relate to figures in the report which are very significant to the present invention. FIG. 1 of the report is also FIG. 2 of the pending Ginsburg patent application, and shows the type of display used herein. The figure shows six frames, three at high contrast and three at low contrast, at low, medium and high spatial frequencies. One of these frames is approximated on the screen of the display unit 10 in FIG. 1 of the present application.

SUMMARY OF THE INVENTION

This invention involves measurement of the visual contrast sensitivity (modulation transfer) function of a human subject by means of a linear or circular spatial frequency pattern on a cathode ray tube whose contrast is automatically decreasing or increasing depending on the subject pressing or releasing a hand-switch button or other response (evoked cortical response). The threshold of detection of the pattern modulation is found by the subject by adjusting the contrast to values which vary about the subject's threshold thereby determining the threshold and also providing by the magnitude of the contrast fluctuations between reversals some estimate of the variability of the subject's absolute threshold. The invention also involves the slow automatic sweeping of the spatial frequency of the pattern over the spatial frequency spectrum of interest; or the stepwise switching to specific selected discrete frequencies after preset time intervals or after threshold has been defined at each frequency by a selected number of subject-determined threshold crossings; i.e., contrast reversals.

The main characteristic of the invention is the automatically decreasing or increasing contrast of the stimulus pattern depending on the actuation of the switch controlled by the subject. The process is the analogue in visual testing to the one introduced in the measurement of auditory acuity by von Bekesy, G. (ACTA OTO-LARYNGOL. 35:411 (1947)) which led to the various types of Bekesy audiometers or automatic audiometers to test hearing. The same advantages with respect to phychophysiological threshold determination as well as speed and economy of threshold measurement, which apply to automatic audiometers, are applied here to the measurement of the visual contrast sensitivity.

The invention provides a simplified method and a new instrument to measure visual contrast sensitivity without the need for a specialized laboratory. It also provides higher speed and economy of threshold measurements.

Accurate determination of visual contrast sensitivity is very important to the Air Force and other armed forces. The invention may be used in test aircraft, flight stress simulators, or centrifuges where limited time is available for such measurements to determine the effects of increased aircraft performance capabilities and/or mission stress on the visual performance of pilots and crew members. The device can quickly evaluate those special characteristics of the human visual system most important in the location of objects in reduced visibility situations such as at night, in weather, or in general smoke and haze. Its speed, accuracy and ease of operation should make it essential in the regular clinical flight examination of all pilots, as the Snellen eye chart for visual acuity is now used.

It is envisioned that visual contrast sensitivity will be used more and more for clinical testing of the general population.

For design and fabrication of the components disclosed, the control voltage values for spatial frequency and contrast of a particular display unit need to be considered. The embodiments disclosed are only some of many possibilities such as microprocessor technology, electronmechanical designs, use of different integrated circuits and combinations of these different approaches.

Thus, while preferred constructional features of the invention are embodied in the structure illustrated herein, it is to be understood that changes and variations may be made by the skilled in the art without departing from the spirit and scope of our invention.

We claim:

1. Visual examination apparatus for measuring visual contrast sensitivity of a subject using a display unit and recording means, the display unit having means to display on a screen a pattern comprising a sequence of light and dark areas at a selected spatial frequency with contrast which varies in accordance with the value of an analog characteristic of a first signal at a first input, said apparatus comprising:

contrast control circuit means having an output coupled to said first input for supplying said first signal, with means for varying said characteristic so that the contrast of said pattern may be automatically varied in an increasing or decreasing direction;

subject response means for developing a response signal having one or the other of two discrete signal states, the state being changeable under control of the subject in attempting to keep the contrast at a threshold level, the subject response means being coupled to the contrast control circuit means so that the direction of change of said characteristic is increasing for one state of said response signal and is decreasing for the other state and the contrast increases or decreases in accordance with the subject's response;

the output of the contrast control circuit means being also coupled to the recording means to record contrast values corresponding to the values of said characteristic at which the response signal changes condition.

2. Visual examination apparatus as recited in claim 1, wherein said subject response means is a switch, and said two discrete signal states are states of the switch in normal and operated positions; and wherein said characteristic of the first signal is a voltage level.

3. Visual examination apparatus as recited in claim 2, wherein said contrast control circuit means is an integrator comprising an operational amplifier having a capacitor connected between the output and the input, resistance means coupling the input of the operational amplifier to one voltage source when said switch is normal and to another voltage source when the switch is operated.

4. Visual examination apparatus as recited in claim 3, including a diode and a Zener diode connected in parallel with said capacitor to set minimum and maximum voltage respectively;

wherein said resistance means includes a resistor from one contact of said switch to the one voltage source, another contact of the switch being connected to the other voltage source, the resistance means also including adjustable resistance means between said one contact of the switch and the input of the operational amplifier to determine the rate of change of the output voltage;

a diode coupling the output of the operational amplifier and said output of the contrast control circuit means, and a resistor connected from the output to a reference voltage point intermediate said one voltage source and said another voltage source.

5. Visual examination apparatus as recited in claim 2, wherein said contrast control circuit means comprises a potentiometer mechanically coupled to a reversing motor, said output being coupled to a sliding contact of the potentiometer, and the switch being coupled to the motor so that the direction of rotation of the motor depends on whether the switch is normal or operated.

6. Visual examination apparatus as recited in claim 1, 2, or 3 wherein said display unit has a second input (F) and said display unit further includes means to select the spatial frequency in accordance with a characteristic of a second signal at said second input;

wherein said apparatus further includes frequency control circuit means having an output coupled to said second input for supplying said second signal, with means for varying said characteristic of the second signal so that the spatial frequency of said pattern may be automatically varied in a predetermined manner to cover a desired spatial frequency bandwidth.

7. Visual examination apparatus as recited in claim 6, wherein said frequency control circuit means comprises means for varying said characteristic of the second signal in a continuous manner so that the spatial frequency is varied in a continuous manner over a predetermined range.

8. Visual examination apparatus as recited in claim 7, wherein said frequency control circuit means is an integrator comprising an operational amplifier having a capacitor connected between the output and input, and a switch across the capacitor for setting the output voltage to an initial value when it is closed.

9. Visual examination apparatus as recited in claim 7, wherein said recording means is an X-Y recorder having X and Y inputs and a recorder stylus, the output of said contrast control circuit means is coupled to the Y input, the output of the frequency control means is coupled to the X input, so that said first and second signals respectively control the Y and X coordinate movements of the recorder stylus, whereby the X coordinate represents both spatial frequency and time with a continuous variation, and the Y coordinate represents contrast, so that the recorder stylus produces a plot which changes vertical direction whenever said subject response means changes state.

10. Visual examination apparatus as recited in claim 9, wherein said frequency control circuit means is an integrator comprising an operational amplifier having a capacitor connected between the output and input, a switch across the capacitor for setting the output voltage to an initial value when it is closed, and input voltage selection means for the operational amplifier.

11. Visual examination apparatus as recited in claim 6, wherein said frequency control circuit means comprises means for changing said characteristic of the second signal in discrete steps so that the spatial frequency changes in discrete steps to predetermined values.

12. Visual examination apparatus as recited in claim 11, wherein said characteristic of the second signal is a voltage value, said means changing said characteristic comprises means for presetting a plurality of discrete voltage values, switching means for selecting the preset voltage values one at a time, and first counting means having successive outputs to set the switching means in a selected sequence.

13. Visual examination apparatus as recited in claim 12, including timing means coupled to said first counting means to advance the count of the first counting means at predetermined time intervals.

14. Visual examination apparatus as recited in claim 12, including second counting means having an input coupled to said subject response means to advance the count of the second counting means after a predetermined number of operations of the subject response means, and the second counting means having an output coupled to said first counting means to advance the count of the first counting means after each occurrence of said predetermined number of operations.

15. Visual examination apparatus as recited in claim 14, having a selector switch associated with the second counting means to select different values for said predetermined number of operations of the subject response means; and also including timing means which may be selected with said selector switch to advance the first said counting means at predetermined time intervals.

16. Visual examination apparatus as recited in claim 1, 2, or 3, wherein said recording means is an X-Y recorder having X and Y inputs and a recorder stylus, the output of said contrast control circuit means is coupled to the Y input, and timing means for providing a time scale is coupled to the X input, so that the Y coordinate represents contrast and so that the recorder stylus produces a plot which changes vertical direction whenever said subject response means changes state.

17. Visual examination apparatus as recited in claim 6, wherein said contrast is varied with a logarithmic scale, and so plotted on the recorder.

* * * * *